(12) United States Patent
Zou et al.

(10) Patent No.: US 11,001,604 B2
(45) Date of Patent: May 11, 2021

(54) METHOD FOR PREPARING TULATHROMYCIN

(71) Applicant: WISDOM PHARMACEUTICAL CO., LTD, Nantong (CN)

(72) Inventors: Ping Zou, Nantong (CN); LingLing Chu, Nantong (CN); Xiaolong Qiu, Nantong (CN); Lin Hu, Nantong (CN); ChengLiang Zhang, Nantong (CN); XiangJun Zeng, Nantong (CN); ShaoHua Gou, Nantong (CN); ZhongPing Wu, Nantong (CN); Wei Shen, Nantong (CN); Jian Fu, Nantong (CN); Ming Xu, Nantong (CN); Ping Wang, Nantong (CN); XinGang Zhang, Nantong (CN); GuangHao Shi, Nantong (CN); JunQiang Wang, Nantong (CN); Jun Chen, Nantong (CN); Lei Cao, Nantong (CN)

(73) Assignee: WISDOM PHARMACEUTICAL CO., LTD., Nantong (CN)

( * ) Notice: Subject to any disclaimer, the term of this patent is extended or adjusted under 35 U.S.C. 154(b) by 0 days.

(21) Appl. No.: 16/764,396

(22) PCT Filed: Feb. 5, 2018

(86) PCT No.: PCT/CN2018/075246
§ 371 (c)(1),
(2) Date: May 15, 2020

(87) PCT Pub. No.: WO2019/119628
PCT Pub. Date: Jun. 27, 2019

(65) Prior Publication Data
US 2020/0354396 A1   Nov. 12, 2020

(30) Foreign Application Priority Data

Dec. 19, 2017   (CN) .......................... 201711371367.4

(51) Int. Cl.
*C07H 1/00*   (2006.01)
*C07H 17/00*   (2006.01)
*C07H 19/24*   (2006.01)

(52) U.S. Cl.
CPC ............... *C07H 19/24* (2013.01); *C07H 1/00* (2013.01); *C07H 17/00* (2013.01)

(58) Field of Classification Search
None
See application file for complete search history.

(56) References Cited

U.S. PATENT DOCUMENTS 6,420,536 B1   7/2002   Bronk et al.

FOREIGN PATENT DOCUMENTS

CN   1259955 A   7/2000
CN   102260306 A   11/2011
(Continued)

*Primary Examiner* — Layla D Berry
(74) *Attorney, Agent, or Firm* — Bayramoglu Law Offices LLC

(57) ABSTRACT

A method for preparing tulathromycin, and two intermediate compounds shown in formula V and formula VI are provided. The method includes the following synthetic route:

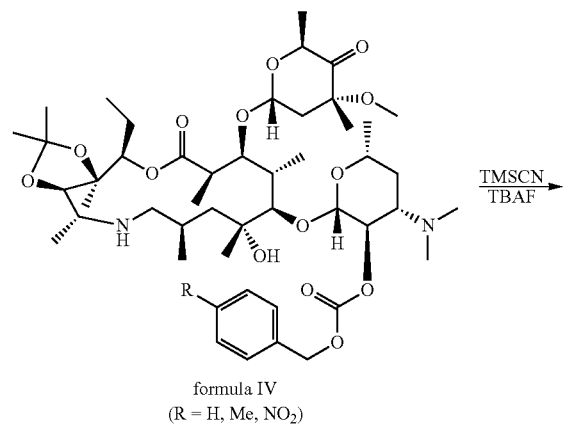

formula IV
(R = H, Me, NO$_2$)

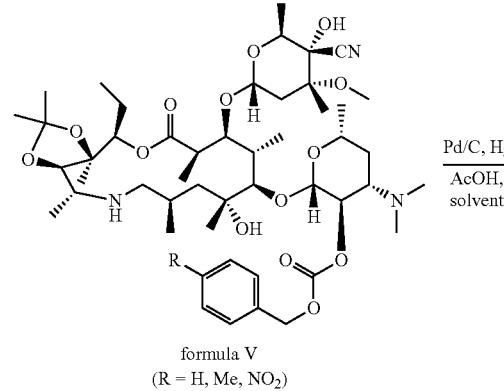

formula V
(R = H, Me, NO$_2$)

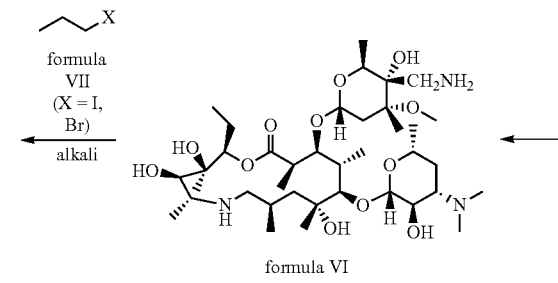

formula VI (Continued)

-continued

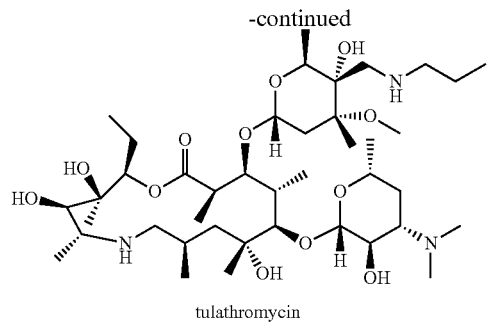

tulathromycin

4 Claims, No Drawings

(56) References Cited

FOREIGN PATENT DOCUMENTS

| | | | |
|---|---|---|---|
| CN | 102295672 A | | 12/2011 |
| CN | 102786569 A | | 11/2012 |
| CN | 103073603 A | | 5/2013 |
| CN | 103588833 A | * | 2/2014 |
| CN | 103864865 A | | 6/2014 |
| CN | 104193789 A | | 12/2014 |
| CN | 104861018 A | | 8/2015 |
| CN | 104876983 A | | 9/2015 |
| CN | 106939029 A | | 7/2017 |
| WO | 9856802 A1 | | 12/1998 |
| WO | 2015014907 A1 | | 2/2015 |

\* cited by examiner

METHOD FOR PREPARING TULATHROMYCIN

CROSS REFERENCE TO THE RELATED APPLICATIONS

This application is the national phase entry of International Application No. PCT/CN2018/075246, filed on Feb. 05, 2018, which is based upon and claims priority to Chinese Patent Application No. 201711371367.4, filed on Dec. 19, 2017, the entire contents of which are incorporated herein by reference.

TECHNICAL FIELD

The present invention relates to the field of chemical synthesis, and more specifically relates to a novel method for preparing tulathromycin.

BACKGROUND

Tulathromycin, as a third-generation macrolide antibiotic, has received widespread attention in the veterinary medicine industry because it requires low concentration during use, shows persistent efficacy, has low minimum inhibitory concentration, functions at a low dosage, is highly soluble in water for injection, is of low cost for overall treatment, and is easily used.

Tulathromycin, with the trade name "Draxxin", is a novel erythromycin semi-synthetic veterinary drug developed by Pfizer, Inc. Animal Health Products Firm in the late 1990s. Tulathromycin is mainly used to treat and prevent respiratory diseases caused by *Actinobacillus pleuropneumonias, Mycoplasma, Pasteurella, Haemophilus parasuis, Bordetella bronchiseptica*, etc. in animals. Tulathromycin was approved for marketing in the European Union by European Union Veterinary Medical Advisory Committee in October 2004, was approved for marketing in the United States by the US FDA in May 2005, and was approved by the Chinese Ministry of Agriculture in the Ministry of Agriculture Announcement No. 957 in 2008, with the dosage form of an injection solution.

Tulathromycin has a complex structure with multiple chiral centers, and contains multiple active groups (including five hydroxyl groups, a macrolide group, and three amine groups). The chemical name of tulathromycin is (2R, 3S, 4R, 5R, 8R, 10R, 11R, 12S, 13S, 14R)-13-[[2',6'-dideoxy-3'-C-methyl-3'-O-methyl-4'-C-[(propylamino) methyl]-α-L-ribo-hexopyranosyl]-oxy]-2-ethyl-3,4,10-trihydroxy-3,5,8,10,12,14-hexamethyl-11-[[3",4",6"-trideoxy-3"-(dimethylamino)-β-D-xylo-hexopyranosyl]oxy]-1-oxa-6-azacyclopentane-15-ketone. Because the compound contains three amine groups, it is weakly electronegative in solution, which is beneficial for penetrating membranes of Gram-negative bacteria and efficiently stimulating the separation of peptidyl tRNA from ribosomes, thus inhibiting the bacterial transpeptidation process, hindering the synthesis and extension of the peptide chain, and thereby affecting the synthesis of bacterial proteins. The chemical structural formula of tulathromycin is as follows:

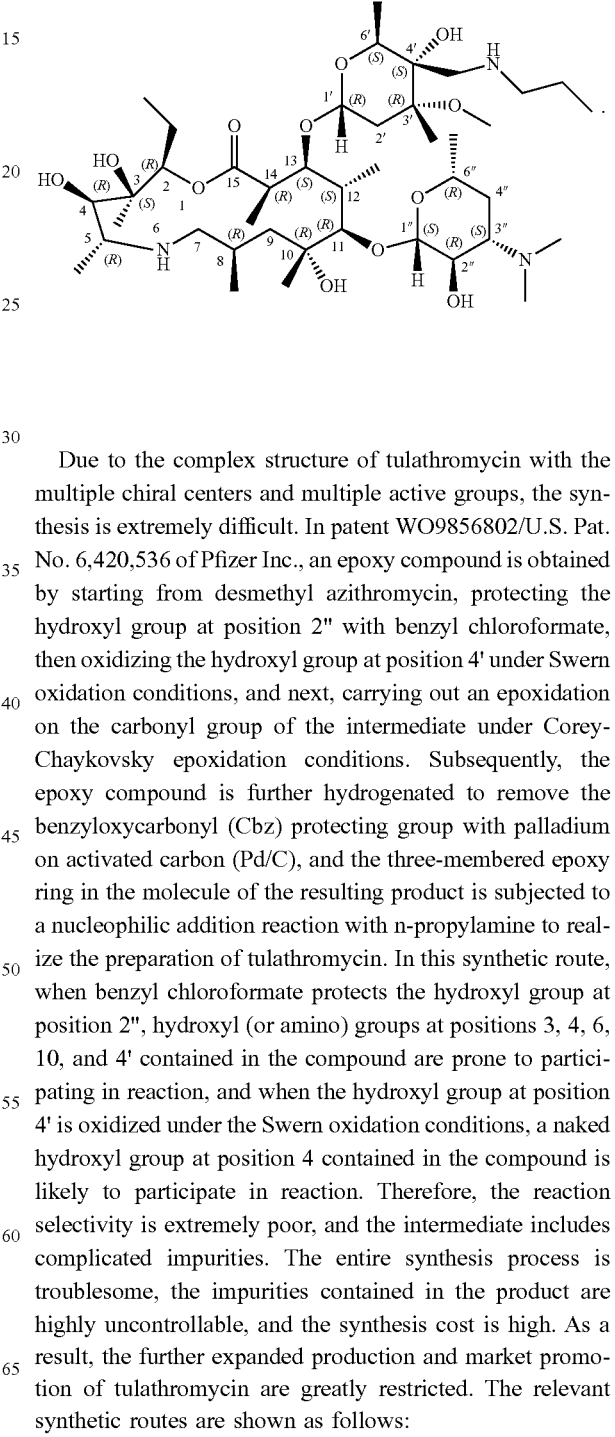

Due to the complex structure of tulathromycin with the multiple chiral centers and multiple active groups, the synthesis is extremely difficult. In patent WO9856802/U.S. Pat. No. 6,420,536 of Pfizer Inc., an epoxy compound is obtained by starting from desmethyl azithromycin, protecting the hydroxyl group at position 2" with benzyl chloroformate, then oxidizing the hydroxyl group at position 4' under Swern oxidation conditions, and next, carrying out an epoxidation on the carbonyl group of the intermediate under Corey-Chaykovsky epoxidation conditions. Subsequently, the epoxy compound is further hydrogenated to remove the benzyloxycarbonyl (Cbz) protecting group with palladium on activated carbon (Pd/C), and the three-membered epoxy ring in the molecule of the resulting product is subjected to a nucleophilic addition reaction with n-propylamine to realize the preparation of tulathromycin. In this synthetic route, when benzyl chloroformate protects the hydroxyl group at position 2", hydroxyl (or amino) groups at positions 3, 4, 6, 10, and 4' contained in the compound are prone to participating in reaction, and when the hydroxyl group at position 4' is oxidized under the Swern oxidation conditions, a naked hydroxyl group at position 4 contained in the compound is likely to participate in reaction. Therefore, the reaction selectivity is extremely poor, and the intermediate includes complicated impurities. The entire synthesis process is troublesome, the impurities contained in the product are highly uncontrollable, and the synthesis cost is high. As a result, the further expanded production and market promotion of tulathromycin are greatly restricted. The relevant synthetic routes are shown as follows:

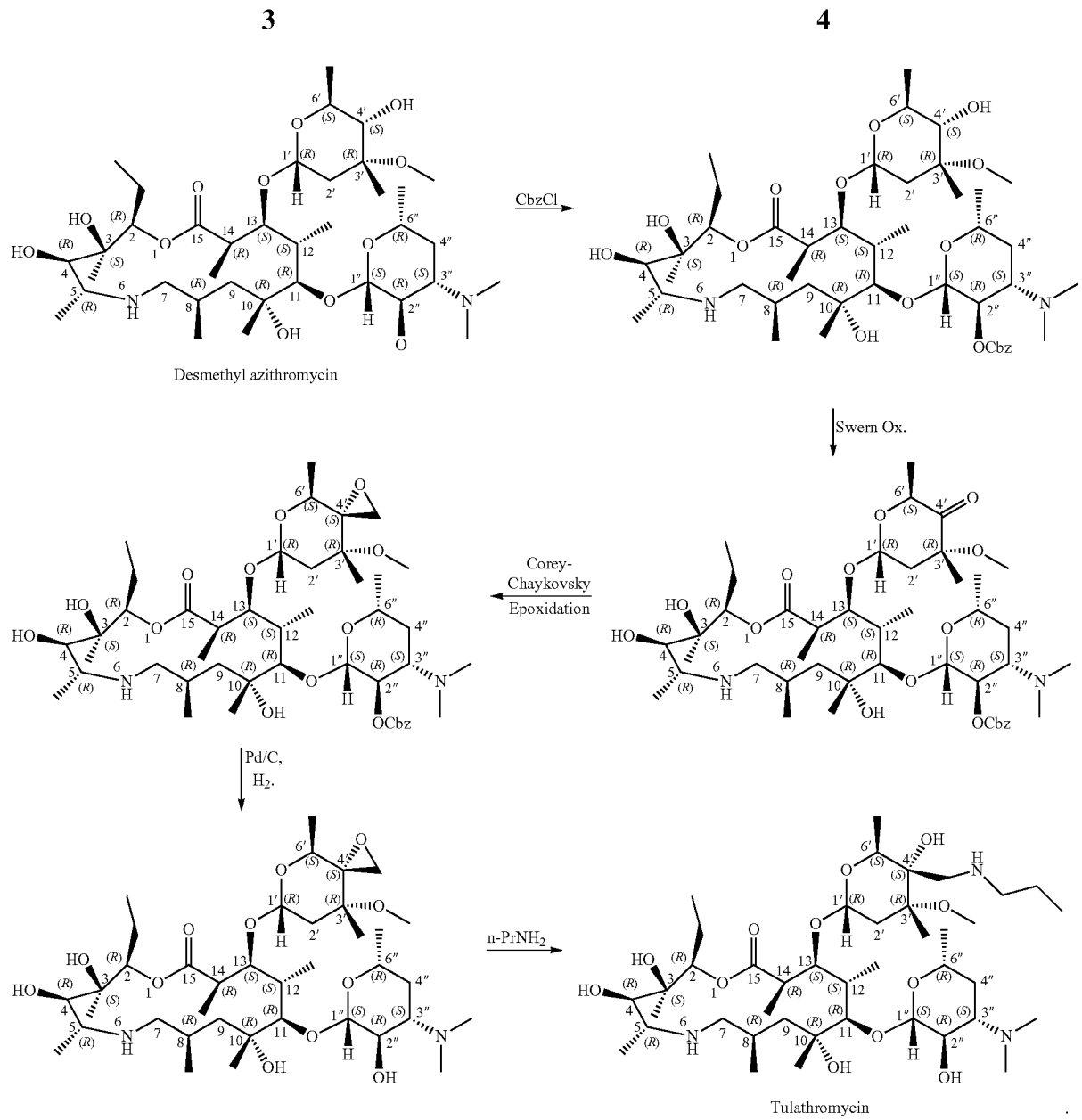

Tulathromycin

The CN102260306 patent reported a preparation of tulathromycin by protecting the hydroxyl group at position 2" and the amino group at position 6 of desmethyl azithromycin with acetyl group, then carrying out an oxidation and epoxidation of the hydroxyl group at position 4', and finally, carrying out a nucleophilic addition on the epoxy at position 4' with n-propylamine after removing the acetyl group by inorganic strong alkali (an alkaline alcohol solution) at high temperature. Because the secondary hydroxyl group at position 4 in the compound is synchronously oxidized during the Swern oxidation, and when the acetyl group on the amino group is removed by using the inorganic strong alkali (an alkaline alcohol solution) at high temperature, the ring is prone to open under the alkaline condition because the macrolide contains lactone, resulting in a large number of by-products and low yield.

The CN102786569 patent realized a preparation of tulathromycin by using the benzyloxycarbonyl (Boc) group to protect both the hydroxyl group at position 2" and the amino group at position 6 of desmethyl azithromycin, then oxidizing the hydroxyl group at position 4', carrying out a deprotection with trifluoroacetic acid and synchronously producing trifluoroacetate, then performing an epoxidation on the carbonyl group at position 4', and finally carrying out a nucleophilic addition of the epoxy with n-propylamine. In this synthetic route, the compound contains a large number of naked active groups during the Corey-Chaykovsky epoxidation, so the reaction is extremely complex, resulting in a large number of impurities after the epoxidation, which is especially difficult to purify.

The CN102295672 patent realized a preparation of tulathromycin by using the Cbz group to first protect the hydroxyl group at position 2" as well, then carrying out a Swern oxidation on the hydroxyl group at position 4', then converting the carbonyl group at position 4' to a methylene group through the methylenation of the carbonyl group, carrying out an epoxidation of the methylene group by hydrogen peroxide, and then carrying out a nucleophilic addition of the epoxy with n-propylamine. In this synthetic route, other active groups of the compound synchronously participate in the competitive reaction when the Cbz group protects the hydroxyl group at 2" position and the hydroxyl group at 4' position is Swern oxidized, resulting in a poor selectivity and a large number of reaction impurities, which is difficult to purify.

Therefore, how to overcome the shortcomings in the prior art for preparing tulathromycin and provide a preparation method that is more suitable for industrial production of tulathromycin has become a problem that needs to be solved in order to realize the further expanded production and market promotion of this product.

SUMMARY

The technical problem to be solved by the present invention is to provide a synthetic method suitable for expanding the production of tulathromycin.

In the method, desmethyl azithromycin (formula I) whose hydroxyl groups at positions 3 and 4 are protected by diisopropylidene is used as a starting material, and the specific reaction formula is as follows:

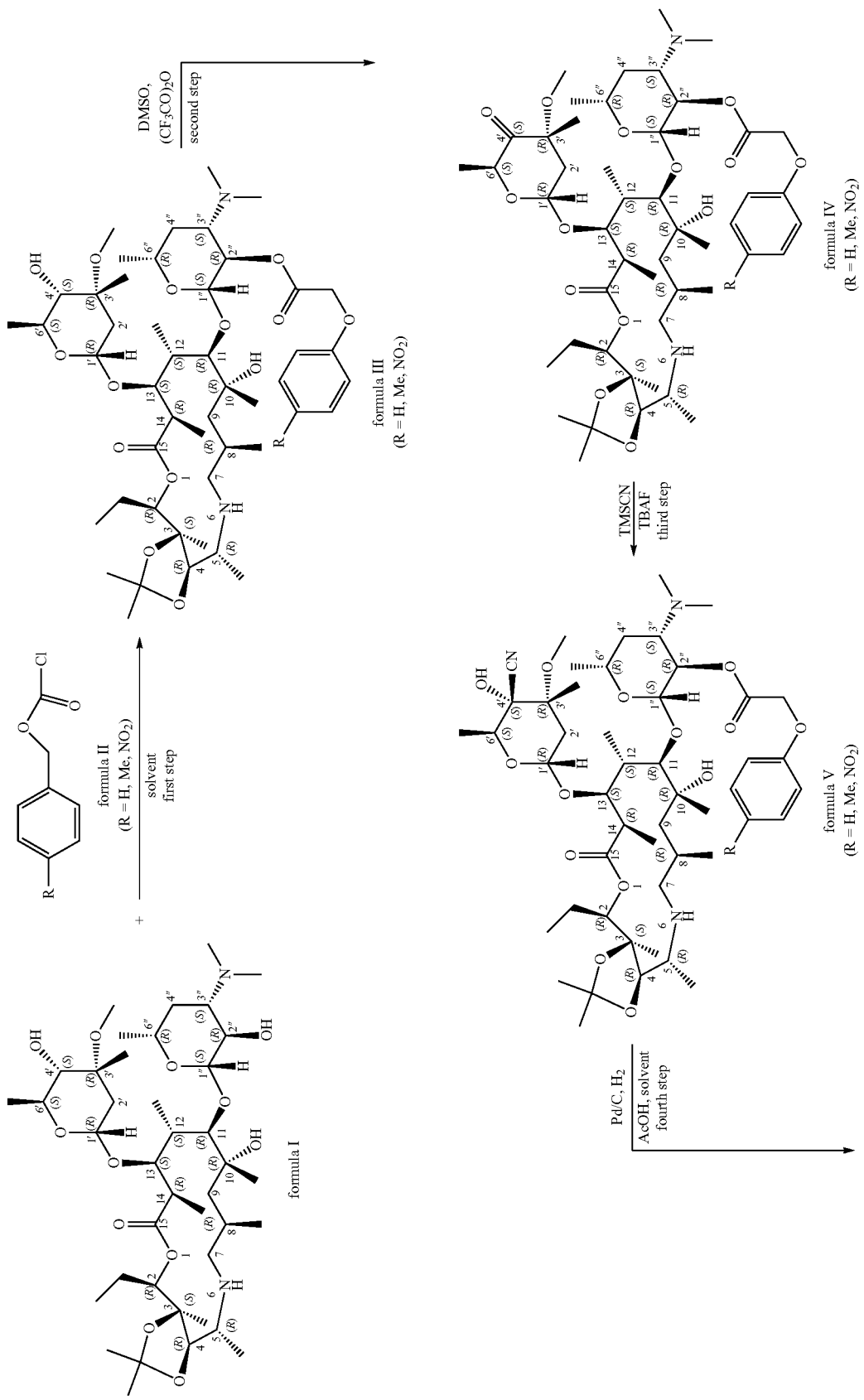

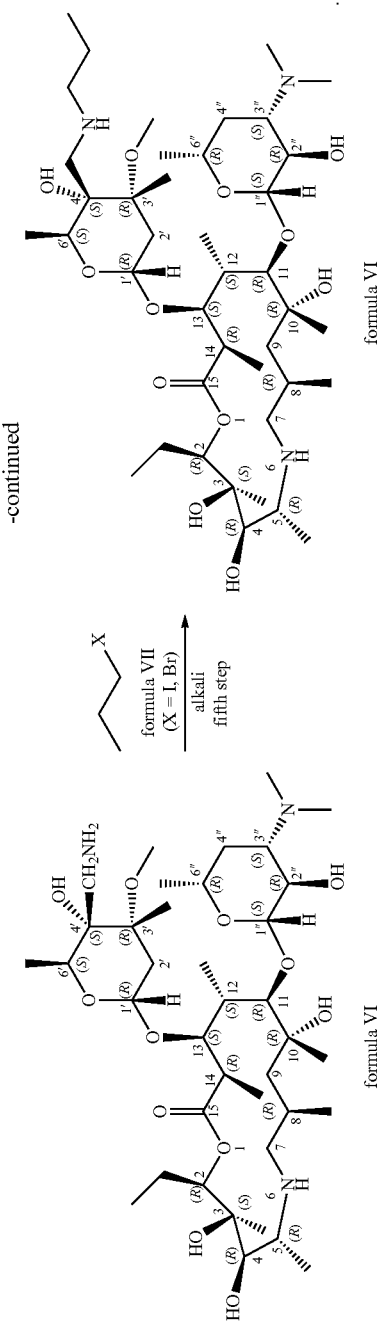

In the first step of the reaction, the desmethyl azithromycin (formula I) whose hydroxyl groups at positions 3 and 4 are protected by diisopropylidene is used as the starting material.

In the first step of the reaction, the compound of formula I reacts with the compound of formula II in the presence of a reaction solvent to protect the hydroxyl group at position 2″ in the compound of formula I, thereby realizing a preparation of the compound of formula III.

The solvent used in the first step of the reaction is at least one selected from the group consisting of tetrahydrofuran (THF), dioxane, $CH_2Cl_2$, $CH_3CN$, and 2-methyltetrahydrofuran (2-MeTHF).

R in formula II is hydrogen (H), methyl (Me), or $NO_2$; and R in formula III is H, Me, or $NO_2$.

In the second step of the reaction, the hydroxyl group at position 4′ in formula III is oxidized to a carbonyl group under Swern oxidation conditions to realize a preparation of the compound of formula IV.

The reagent used in the second step of Swern reaction is dimethyl sulfoxide (DMSO) and $(CF_3CO)_2O$.

R in formula IV is H, Me, or $NO_2$.

In the third step of the reaction, the cyano group of trimethylsilyl cyanide (TMSCN) is used to carry out an additional reaction on the carbonyl group at position 4′ in the compound of formula IV under an action of tetrabutylammonium fluoride (TBAF) to realize a preparation of the compound of formula V.

The solvent used in the fourth step is at least one selected from the group consisting of THF, 2-MeTHF, $CH_2Cl_2$, dioxane and $CH_3CN$.

R in formula V is H, Me, or $NO_2$.

In the fourth step of the reaction, a hydrogenation of the compound of formula V is carried out in the presence of acetic acid (HOAc) under a condition of Pd/C as a catalyst to hydrogenate the cyano group in the compound to an aminomethyl group, and synchronously remove the protecting group of the hydroxyl group at position 2′ and the diisopropylidene protecting the hydroxyl groups at positions 3 and 4 to realize a preparation of the compound of formula VI.

A hydrogen pressure used in the fourth step ranges from 2 atm to 10 atm.

The solvent used in the fourth step is at least one selected from the group consisting of methanol (MeOH), ethyl alcohol (EtOH), and isopropyl alcohol (i-PrOH).

In the fifth step of the reaction, the compound of formula VI reacts with 1-halogenated propane (formula VII) under an action of an alkali to realize a preparation of tulathromycin.

The alkali used in the fifth step is at least one selected from the group consisting of 4-dimethylaminopyridine (DMAP), triethylamine ($Et_3N$), $Na_2CO_3$, $Cs_2CO_3$, $K_2CO_3$, and N,N-Diisopropylethylamine (DIPEA).

X in formula VII is iodine (I) or bromine (Br).

Since the active hydroxyl groups at position 3 and 4 in the starting material are protected by diisopropylidene, this synthetic route avoids the main side reactions in the process of oxidation and epoxidation, has good selectivity, is easy to obtain high purity products and realize industrial production, and has obvious advantages compared with existing synthetic routes.

DETAILED DESCRIPTION OF THE EMBODIMENTS

The present invention can be more specifically understood through the following embodiments, but it is illustrative rather than limiting the scope of the present invention.

EMBODIMENTS

Embodiment 1. Preparation of the Compound of Formula III (R=Me)

The compound of formula I (500 g, 645.16 mmol) and $CH_2Cl_2$ (3.5 L) were added to a 10 L four-neck flask. The system was fully stirred, and then the temperature of the system was maintained at about 20° C. p-methylbenzyl chloroformate (formula II, R=Me, 180 g, 975 mmol) was slowly added dropwise to the reaction system through a dropping funnel, and the temperature of the system was maintained at about 20° C. during the dropwise addition. After the dropwise addition was completed, the system reacted at the temperature for 3 hours. Then, the system was slowly added with 4 L of saturated aqueous sodium hydrogen carbonate solution to quench the reaction. After the addition was complete, the system was stirred at room temperature for 2 hours. The system was set aside for 2 hours and then separated. The organic phase was washed with 1 L of water, and then the organic phase was added with 250 g of anhydrous sodium sulfate and stirred to dry. Filtration and reduced pressure concentration of the organic phase were performed until no obvious cut fractions were produced to obtain the compound of formula III (R=Me, oily matter, 636 g, the product was used directly in the subsequent step without purification).

Embodiment 2. Preparation of the Compound of Formula IV (R=Me)

The compound of formula III (R=Me, 600 g) obtained in Embodiment 1 and anhydrous $CH_2Cl_2$ (2.5 L) were added to a 10 L four-necked flask. The system was subjected to nitrogen gas replacement three times, and the subsequent addition process was protected with nitrogen. Anhydrous DMSO (1.2 L) was added to the reaction system, the temperature of the system was reduced to −70° C. with stirring, and then trifluoroacetic anhydride (410 g) was slowly added through a dropping funnel at the temperature of about −70° C. After the addition was completed, the system was stirred for 1.5 hours at the temperature. Then, triethylamine (270 g) was slowly added dropwise through the dropping funnel. After the addition was completed, the system was stirred and reacted for 1.5 hours, and then $H_2O$ (3 L) was slowly added through the dropping funnel. After the system was slowly heated to about 20° C. and stirred for 1 hour, the system was set aside for 2 hours, and then the organic phase was separated. The organic phase was washed once with $H_2O$ (1.5 L), and then the organic phase was separated. The organic phase was concentrated under reduced pressure until no obvious cut fractions were produced, and then was concentrated again with 1 L of isopropyl alcohol until no obvious cut fractions were produced. The residue was added with 0.5 L of isopropyl alcohol and heated to dissolve. After being dissolved, the system was slowly cooled to about −10° C. under stirring overnight, and then filtered to obtain a solid. The solid was dried to obtain the compound of formula IV (R=Me, 389 g, and the yield in the two steps was 69%).

Embodiment 3. Preparation of the Compound of Formula V (R=Me)

The compound of formula IV (R=Me, 120 g, 130 mmol) obtained in Embodiment 2 was added to a 2 L reaction flask. $CH_2Cl_2$ (1 L) was added to the system. After the system was stirred and dissolved, the system was cooled to about 0° C., and then trimethylsilyl cyanide (15.5 g, 156 mmol) was slowly added through a dropping funnel. After the dropwise addition was completed, the temperature of the system naturally raised to room temperature and reacted overnight. Then, TBAF (1 M in THF, 160 mL) was slowly added to the system, and reacted at the temperature for 5 hours after the dropwise addition was completed. The reaction system was quenched by slowly adding $H_2O$ (500 mL). The system was placed to separate into layers and obtain the organic phase. The organic phase was washed twice with a saturated sodium chloride solution (2×500 mL) and then dried with anhydrous sodium sulfate. After filtration, the organic phase was concentrated under reduced pressure until no obvious cut fractions were produced. The residue was dissolved by adding ethyl acetate (35 mL), then added with n-heptane (250 mL), and was heated to 70-80° C. to dissolve completely. Subsequently, the temperature was slowly reduced to −5° C., and the solution was stirred for 12 hours, and suction filtered to obtain a product. Then, the product was vacuum dried to obtain the compound of formula V (R=Me, 92 g, 75%).

Embodiment 4. Preparation of the Compound of Formula VI

The compound of formula V (R=Me, 52 g, 55 mmol) obtained in Embodiment 3 was added to 2 L autoclave, then methanol (500 mL) and HOAc (150 mL) were added. After stirring and dissolving completely, Pd/C (8 g, 10%) was added under the protection of nitrogen. The system was subjected to nitrogen gas replacement for 3 times and hydrogenated at 35° C. and 5 atm for 12 hours. After the reaction was completed, the reaction solution was taken out and filtered. The filter cake was washed with methanol (100 mL). The filtrate was collected and concentrated with no obvious cut fractions. The residue was added with ethyl acetate (30 mL), stirred and dissolved completely. Then, heptane (150 mL) was slowly added dropwise, and stirred for 3 hours. A large number of white solids were precipitated in the system, and then filtered to obtain a filter cake. The filter cake was washed with a small amount of cooled heptane and then dried to obtain the compound of formula VI (34.5 g, 82%).

Embodiment 5. Preparation of Tulathromycin

The compound of formula VI (22 g, 28.8 mmol), DMAP (3.5 g), and $CH_2Cl_2$ (80 mL) were added to a 500 mL reaction flask. After stirring and dissolving completely, the temperature of the system was reduced to 0° C. The $CH_2Cl_2$ solution (5 mL) containing 1-iodopropane (5.5 g) was slowly added dropwise through a dropping funnel, and the temperature of the system was kept at about 0° C. during the dropwise addition. The temperature of the system naturally raised to room temperature and the system reacted with stirring for 5 hours. The reaction was quenched by adding $H_2O$ (50 mL). The organic phase was separated, and the water phase was extracted with $CH_2Cl_2$ (2×30 mL). The organic phase was collected and washed twice with a saturated sodium chloride solution (2×40 mL). Then, the organic phase was desolvated under reduced pressure with no obvious cut fractions. The system was desolvated by adding n-heptane (50 mL) with no obvious cut fractions. Subsequently, the residue was added with ethyl acetate (12 mL) and stirred, and then n-heptane (90 mL) was added. The system was heated to 70-80° C. and stirred to dissolve completely. Then, the system was slowly cooled to about −5° C., stirred for 5 hours, and suction filtered to obtain a solid. The obtained solid was vacuum dried at 40° C. to obtain tulathromycin (white solid, 18.2 g, 78%).

Embodiment 6. Preparation of the Compound of Formula III (R=NO₂)

The compound of formula I (50.0 g, 64.5 mmol) and $CH_2Cl_2$ (300 mL) were added to a 1000 ml four-neck flask. The system was fully stirred to dissolved completely. p-nitrobenzyl chloroformate (formula II, R=NO$_2$, 18.0 g, 83.5 mmol) was slowly added dropwise to the reaction system through a dropping funnel at a temperature of about 20° C. The temperature of the system was maintained at about 20±5° C. during the dropwise addition. After the dropwise addition was completed, the system reacted at the temperature for 5 hours. Then, the system was slowly added with saturated aqueous sodium hydrogen carbonate solution (250 mL) to quench the reaction. After the addition was complete, the system was stirred at room temperature for 2 hours and then separated. The organic phase was washed with saturated sodium chloride solution (100 mL), and then the organic phase was dried by adding anhydrous sodium sulfate. Filtration and high vacuum reduced pressure concentration of the organic phase were performed until no obvious cut fractions were produced to obtain the compound of formula III (R=NO$_2$, 60.2 g, the product was used directly in the subsequent step without purification).

Embodiment 7. Preparation of the Compound of Formula IV (R=NO₂)

The compound of formula III (R=NO$_2$, 52 g) obtained in Embodiment 6 and anhydrous $CH_2Cl_2$ (200 mL) were added to a 1 L four-necked flask. The reaction system was added with anhydrous DMSO (105 mL) under the protection of nitrogen. The temperature of the system was reduced to −75° C. with stirring, and then trifluoroacetic anhydride (36 g) was slowly added through a dropping funnel. The temperature of the system was maintained between −70° C. and −75° C. during the dropwise addition. After the dropwise addition was completed, the system was stirred for 1.5 hours at the temperature. Then, triethylamine (24 g) was slowly added dropwise through the dropping funnel. After the dropwise addition was completed, the system was stirred and reacted for 1.5 hours at the temperature, and then $H_2O$ (250 mL) was slowly added dropwise through the dropping funnel. After the system was slowly heated to about 20° C. and stirred for 1 hour, the system was placed and the organic phase was separated. The organic phase was washed once with $H_2O$ (120 mL), and then the organic phase was separated. The organic phase was concentrated under reduced pressure with no obvious cut fractions, and then was concentrated again with isopropyl alcohol (80 mL) with no obvious cut fractions. The residue was added with isopropyl alcohol (40 mL) and heated to dissolve. After being dissolved, the system was slowly cooled to about −10° C. under stirring overnight, and then filtered to obtain a solid. The solid was dried to obtain the compound of formula IV (R=NO₂, 31.1 g, and the yield in the two steps is 59%).

Embodiment 8. Preparation of the Compound of Formula V (R=NO₂)

The compound of formula IV (R=NO₂, 25 g, 26.3 mmol) obtained in Embodiment 7 was added to a 500 mL reaction flask. CH₂Cl₂ (180 mL) was added to the system. After the system was stirred and dissolved, the system was cooled to about 0° C. in an icy salt bath, and then trimethylsilyl cyanide (3.3 g, 33.3 mmol) was slowly added through an injection syringe. After the injection was completed, the temperature of the system naturally raised to room temperature and reacted overnight. Then, TBAF (1 M in THF, 35 mL) was slowly added dropwise to the system, and reacted at the temperature for 3 hours after the dropwise addition was completed. The reaction system was quenched by slowly adding H₂O (100 mL). The system was placed to separate into layers and obtain the organic phase. The organic phase was washed twice with a saturated sodium chloride solution (2×80 mL) and then dried with anhydrous sodium sulfate. After filtration, the organic phase was concentrated under reduced pressure with no obvious cut fractions. The residue was dissolved by adding ethyl acetate (7 mL), then added with n-heptane (50 mL), and was heated to about 75° C. to dissolve completely. Subsequently, the temperature was slowly reduced to −5° C., and the solution was stirred for 12 hours, and suction filtered to obtain a product. Then, the product was vacuum dried to obtain the compound of formula V (R=NO₂, 20.2 g, 78%).

Embodiment 9. Preparation of the Compound of Formula VI

The compound of formula V (R=NO₂, 16 g, 16.3 mmol) obtained in Embodiment 8 was added to 500 mL minitype autoclave, then isopropanol (120 mL) and HOAc (45 mL) were added. After stirring and dissolving completely, Pd/C (2.5 g, 10%) was added under the protection of nitrogen. The system was subjected to nitrogen gas replacement for 3 times and hydrogenated at 35° C. and 5 atm for 24 hours. After the reaction was completed, the reaction solution was taken out and filtered twice with a Buchner funnel. The filter cake was washed with isopropanol (20 mL). The filtrate was collected and concentrated under high vacuum reduced pressure with no obvious cut fractions. The residue was added with ethyl acetate (10 mL), stirred and dissolved completely. Then, heptane (50 mL) was slowly added dropwise, and stirred overnight. A large number of white solids were precipitated in the system, and then filtered to obtain a filter cake. The filter cake was washed with a small amount of cooled heptane and then dried to obtain the compound of formula VI (9.2 g, 73.9%).

Embodiment 10. Preparation of Tulathromycin

The compound of formula VI (8.6 g, 11.3 mmol), DIPEA (1.5 g, 11.6 mmol), and CH₂Cl₂ (30 mL) were added to a 200 mL reaction flask. After stirring and dissolving completely, the temperature of the system was reduced to 0° C. The CH₂Cl₂ solution (2 mL) containing 1-iodopropane (1.4 g, 11.4 mmol) was slowly added dropwise through an injection syringe, and the temperature of the system was kept at about 0° C. during the dropwise addition. After the dropwise addition was completed, NaI (100 mg) was added to the system. The temperature of the system naturally raised to room temperature and the system reacted with stirring for 12 hours. The reaction was quenched by adding H₂O (20 mL). The organic phase was separated, and the water phase was extracted with CH₂Cl₂ (2×30 mL). The organic phase was collected and washed twice with a saturated sodium chloride solution (2×40 mL). Then, the organic phase was desolvated under reduced pressure with no obvious cut fractions. The system was desolvated by adding n-heptane (30 mL) with no obvious cut fractions. Subsequently, the residue was added with ethyl acetate (5 mL) and stirred, and then n-heptane (35 mL) was added. The system was heated to 70-80° C. and stirred to dissolve completely. Then, the system was slowly cooled to about −5° C., stirred for 5 hours, and suction filtered to obtain a solid. The obtained solid was vacuum dried at 40° C. to obtain tulathromycin (white solid, 5.86 g, 64.3%).

What is claimed is:
1. A method for preparing tulathromycin, comprising the following synthetic route:

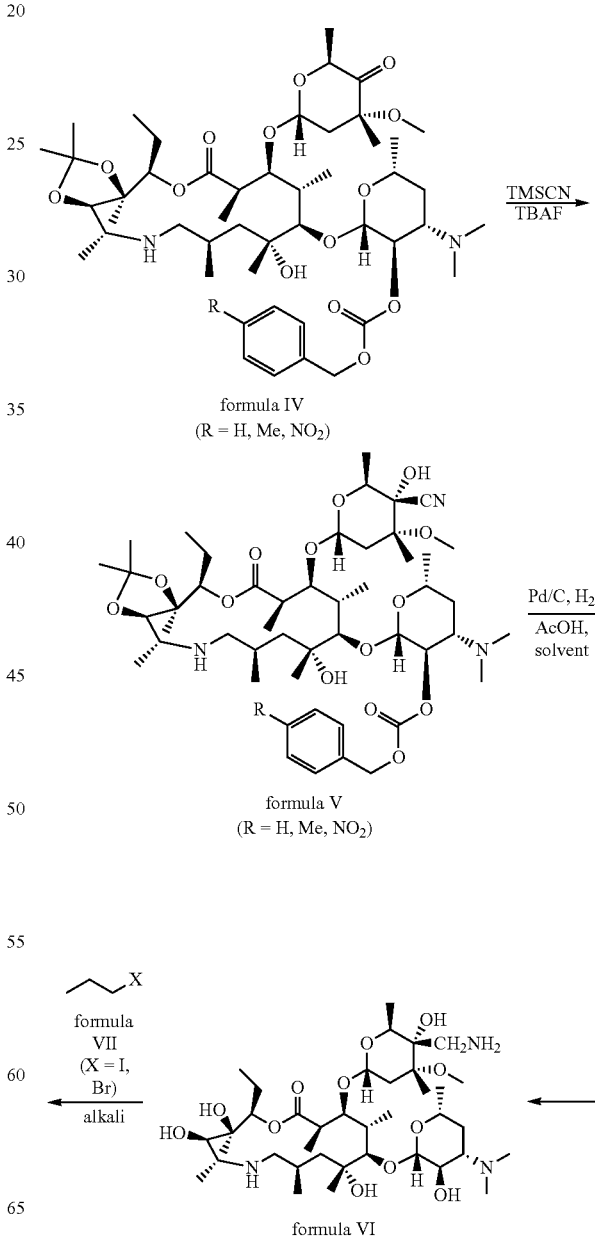

-continued

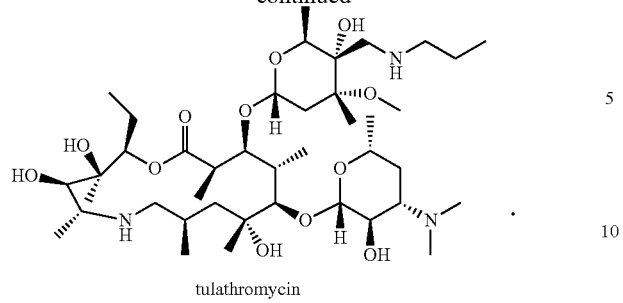

tulathromycin

2. A compound having the chemical structure of formula V according to claim 1.

3. The compound having the chemical structure of formula V according to claim 2, wherein the compound is obtained by reacting the compound of formula IV with the trimethylsilyl cyanide (TMSCN) under an action of the tetrabutylammonium fluoride (TBAF), wherein R in formula IV is hydrogen (H), methyl (Me), or nitrogen dioxide ($NO_2$), and R in formula V is H, Me, or $NO_2$.

4. The method according to claim 1, wherein the tulathromycin is obtained by reacting the compound of formula VI with the compound of formula VII under an action of the alkali, the alkali is at least one selected from the group consisting of 4-dimethylaminopyridine (DMAP), triethylamine ($Et_3N$), $Na_2CO_3$, $Cs_2CO_3$, $K_2CO_3$, and N,N-Diisopropylethylamine (DIPEA), and X in formula VII is iodine (I) or bromine (Br).

* * * * *